United States Patent [19]

Morris, Jr. et al.

[11] Patent Number: 5,496,569

[45] Date of Patent: Mar. 5, 1996

[54] SIMULTANEOUS TREATMENT OF OSTEOPOROSIS AND HYPERTENSION WITH POTASSIUM BICARBONATE

[75] Inventors: R. Curtis Morris, Jr.; Anthony Sebastian, both of San Francisco, Calif.

[73] Assignee: The Regents of the University of California, Oakland, Calif.

[21] Appl. No.: 42,309

[22] Filed: Apr. 2, 1993

Related U.S. Application Data

[63] Continuation-in-part of Ser. No. 420,597, Oct. 17, 1989, Pat. No. 5,171,583, which is a continuation-in-part of Ser. No. 260,856, Oct. 21, 1988, abandoned.

[51] Int. Cl.$^6$ .............................. A01N 59/00; A61K 33/00
[52] U.S. Cl. ............................................. 424/717; 424/722
[58] Field of Search ............................ 424/717, 722

[56] References Cited

U.S. PATENT DOCUMENTS

| | | | |
|---|---|---|---|
| 4,289,750 | 9/1981 | Kopp et al. | 424/33 |
| 4,851,221 | 7/1989 | Pak et al. | 424/693 |
| 5,171,583 | 12/1992 | Morris, Jr. et al. | 424/717 |

OTHER PUBLICATIONS

Overlack et al Klin Wochenschr. 1985 63:352–360.

*Primary Examiner*—Peter F. Kulkosky
*Attorney, Agent, or Firm*—Townsend and Townsend and Crew

[57] ABSTRACT

A method for simultaneously treating osteoporosis and hypertension in the same individual by the administration of pharmaceutically acceptable alkalinizing potassium salts, such as potassium bicarbonate, preferably in the form of a dietary supplement.

9 Claims, 8 Drawing Sheets

KHCO3 in Postmenopausal Women
Effect on Blood Pressure and Urine Calcium

SIMULTANEOUS TREATMENT OF OSTEOPOROSIS AND HYPERTENSION WITH POTASSIUM BICARBONATE

Government Support

The U.S. government may have certain rights in the invention pursuant to Grant No. NS-23780 awarded by the National Institutes of Health.

This is a continuation-in-part of U.S. application Ser. No. 420,597, filed on Oct. 17, 1989, now U.S. Pat. No. 5,171,583 granted Dec. 15, 1992, which was a continuation-in-part of U.S. application Ser. No. 260,856, filed Oct. 21, 1988, now abandoned.

FIELD OF THE INVENTION

This invention concerns novel methods for simultaneously treating osteoporosis and hypertension in the same individual and, more particularly, involves the administration for such purpose of pharmaceutically acceptable alkalinizing potassium salts, such as potassium bicarbonate.

BACKGROUND OF THE INVENTION

Osteoporosis is a metabolic bone disease characterized pathologically by an absolute decrease in the amount of bone, and clinically by increased susceptibility to fractures. Hypertension is an insidious disease in which the blood pressure of an individual is abnormally increased.. It is clinically recognized as an elevation of systolic arterial blood pressure of 150 mm Hg or greater and/or elevation of diastolic arterial blood pressure of 90 mm Hg or higher.

Calcium bone deficiency is believed to be one of the factors which contributes to the pathogenesis of osteoporosis. Riggs, in Cecil Textbook of Medicine, Ed(s) Wyngaarden et al., (1985), p. 1456; Nordin, (1985), Lancet 2:720; Fujita, (1986), *Mineral Electrolyte Metab.* 12:149–156; Heaney, in Osteoporosis II Ed(s), Bonzel, (1979), p. 101; and Heaney, (1982), *J. Lab. Clin. Med.* 100:309. On the other hand, it has long been recognized that the blood pressure of a substantial proportion of those patients afflicted with "essential hypertension" (hypertension whose cause is not readily apparent) may be reduced by restriction of dietary sodium chloride. Simpson, F.O. in *Hypertension: Pathophysiology, Diagnosis, and Management*, Eds. Laragh et al. (1990), pp. 205–215. Treatment of persons suffering from both osteoporosis and hypertension is thus complicated by the need to increase calcium bone retention to ameliorate the osteoporosis and the desirability of decreasing sodium and chloride retention to ameliorate hypertension.

Diuretic agents, a mainstay in anti-hypertensive therapy, increase urinary output and the excretion of sodium and chloride ions, but have variable effects on other ions, such as calcium, in some cases increasing calcium excretion. Friedler (1987), *Mediguide to Nephrology* 1:1–8. To administer diuretic agents to treat hypertension in a patient with osteoporosis or susceptible to osteoporosis may thus detrimentally affect the retention of bone calcium in the patient.

On the other hand, the thiazide group of diuretic agents, exemplified by hydrochlorothiazide, tend to reduce urine calcium excretion and have been described as potentially useful in the treatment of both hypertension and osteoporosis in the same individual. While several investigators have reported findings suggestive of a potential role for thiazide in the prevention of osteoporosis (Wasnich (1983), *N. Engl. J. Med.* 309:344–347; Wasnich (1986), *Obstetrics and Gynecology* 67:457–462; Wasnich (1990), *Br. Med. J.* 301:1303–1305; LaCroix (1990), *N. Engl. J. Med.* 322:286–290), others have reported studies indicating that thiazides increase the risk of hip fractures (Heidrich (1991), *Ann. Int. Med.* 1.15:1–6) or do not significantly reduce the risk of bone fractures (Adland-Davenport (1985), *Am. J. Obstet. Gynecol.* 15.2:630–634). A review of the literature on thiazides and osteoporosis concluded that "it is still premature to prescribe the thiazides for osteoporosis" (Ray 1991), *Ann. Int. Med.* 15:64–5).

Several other non-diuretic anti-hypertensive agents do not negatively affect calcium retention, but neither do they improve calcium retention. There is thus a continuing need for a single therapeutic agent to simultaneously treat both osteoporosis and hypertension in the same individual.

In U.S. patent application Ser. No. 260,856 filed Oct. 21, 1988, and now abandoned, we have disclosed that non-halide alkalinizing potassium salts may be used in the treatment of either osteoporosis or hypertension. A continuation-in-part of the aforesaid application, Ser. No. 420,597 filed Oct. 17, 1989, which claims the use of such salts in treating osteoporosis, has matured into U.S. Pat. No. 5,171,583 granted Dec. 15, 1992. Another continuing application of said Ser. No. 260,856, Ser. No. 708,827, filed May 29, 1991, claims administering such salts to treat hypertension.

As discussed above, thiazide diuretics used in the treatment of hypertension also reduce urine calcium excretion and might, therefore, be expected to be useful in the treatment of osteoporosis. However, some studies have shown that thiazides do not in fact provide protection against osteoporosis and may rather increase the risk of bone fractures. As the thiazide diuretics illustrate by way of analogy, prior to the present invention one could not preclude the possibility that the presence of osteoporotic disease in an individual might adversely influence that individual's ability to respond to the blood pressure-lowering effect of an alkalinizing salt of potassium. Similarly, the possibility that essential hypertension in an individual would adversely influence that individual's ability to respond to the bone-conserving effect of an alkalinizing potassium salt could not be excluded. Accordingly, prior to this invention it would not have been expected that a non-halide alkalinizing potassium salt which is effective in treating hypertension in one group of individuals and in treating osteoporosis in another group of individuals, will be effective in treating both hypertension and osteoporosis in the same individual.

SUMMARY OF THE INVENTION

The present invention involves a novel method for simultaneously treating both osteoporosis and hypertension in the same individual, by administering a therapeutically- or prophylactically-effective amount of a pharmacologically-acceptable alkalinizing potassium salt of a non-halide anion capable of reducing the acidity of tissue fluids or urine and mixtures thereof. The potassium salt may be selected from the group consisting of potassium bicarbonate and a potassium salt of a carboxylic acid, e.g., potassium gluconate or potassium citrate, which is metabolized to bicarbonate in vivo. Potassium bicarbonate is particularly preferred.

The non-halide potassium salt may be administered to ameliorate or prevent osteoporosis and hypertension in any of several therapeutically- or prophylactically-acceptable forms and by a variety of routes. Such compositions are most conveniently formulated and administered as a dietary supplement. An effective dosage of potassium bicarbonate, for example, is typically about 30–180 mmoles per 60 kg body weight per day.

The method of the invention is particularly useful in the treatment of patients on nutritionally adequate whole-food diets that have "normal" salt (NaCl) contents (about 75 to 300 meq. of sodium per day). Since the treatment hereof is effective in patients on such normal salt diets it is unnecessary to require restriction of salt intake, a major problem in achieving patient compliance with other modalities.

DETAILED DESCRIPTION OF THE INVENTION

Figure 1:
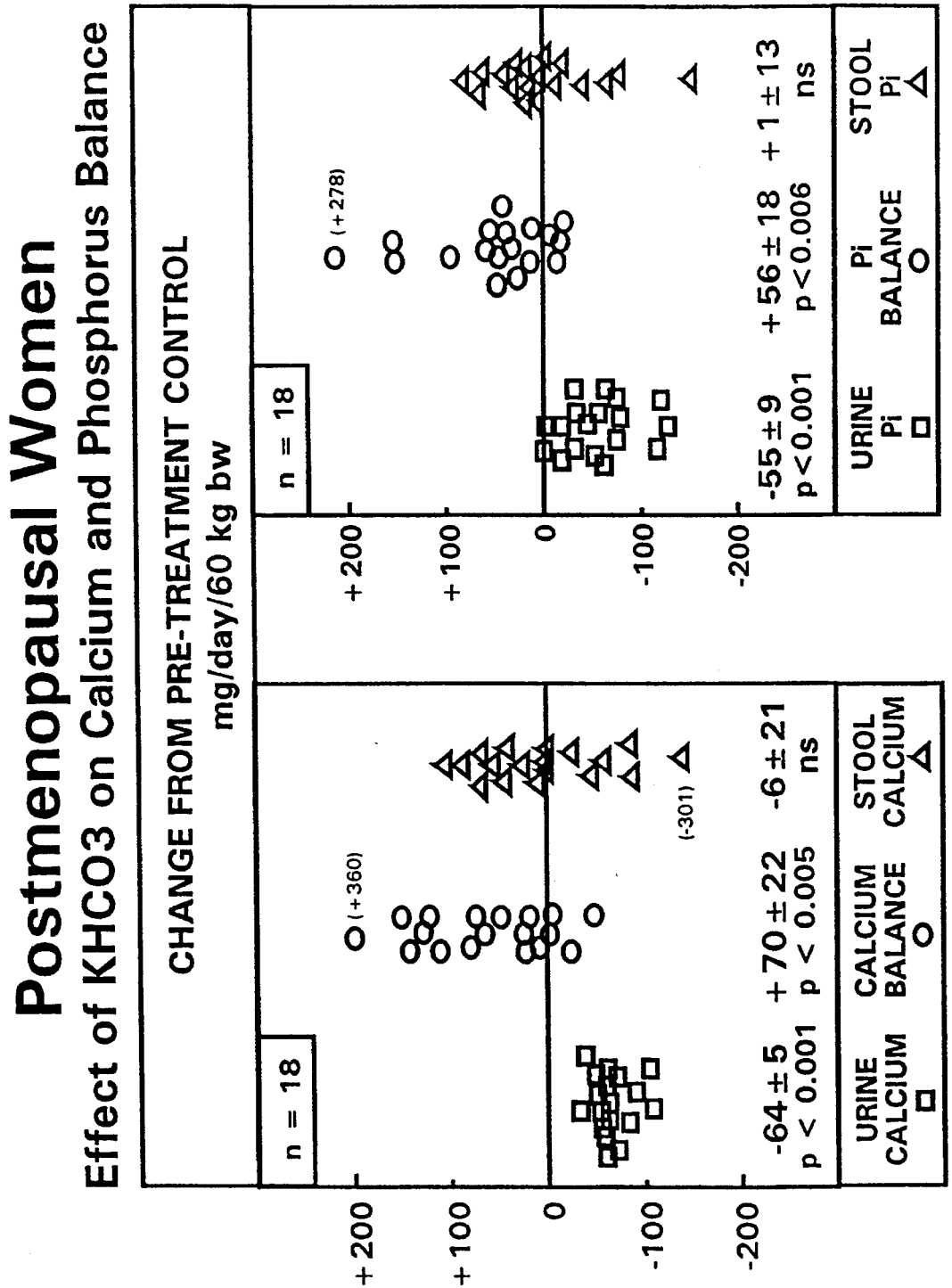
FIG. 1 is a graph showing urine calcium and phosphorus excretion, calcium and phosphorus balance, and stool calcium and phosphorus excretion, expressed as the change from the corresponding pre-treatment control values, resulting from the administration of 60–120 mmoles of potassium bicarbonate per 60 kg body weight per day for 18 days to 18 postmenopausal normotensive female subjects.

As used herein, the terms "treatment" or "treating" relate to any simultaneous treatment of osteoporotic and hypertensive diseases, and include: (1) preventing osteoporosis and hypertension from occurring in a subject who may be predisposed to these diseases but who has not yet been diagnosed as having them; (2) inhibiting these diseases, i.e., arresting their development; or (3) ameliorating or relieving the symptoms of these diseases, i.e., causing regression of the osteoporotic and hypertensive states. With respect to osteoporotic disease, the treatment of the invention reduces the subject's calcium excretion and thereby improves calcium balance, decreases bone resorption and conserves and/or increases bone mass. In the case of hypertension, the treatment reduces the subject's systolic, diastolic and/or mean arterial blood pressure.

The non-halide alkalinizing potassium salts which may be employed in the process of the present invention are those which produce the foregoing results without significant undesirable side effects. By an "alkalinizing salt" is meant one which, when present in the body fluids, produces hydroxyl ions or consumes hydroxyl ions and is thereby capable of reducing the acidity of tissue fluids or urine. A number of pharmaceutically-acceptable alkalinizing potassium salts are known, several of which are set forth in Berg et al., *J. Pharmaceut. Sci.* (1977) 66:1, which is incorporated herein by reference. Given the disclosure herein, it will be well within the ability of one skilled in the art to select and screen pharmaceutically-acceptable alkalinizing salts for simultaneously treatment of osteoporosis and hypertension. Desirably, a salt will be selected which is therapeutically effective in amounts readily achievable in humans while being relatively well tolerated. Different salts may be chosen depending on particular routes of administration and preferred modes of formulation. Additionally, it may be preferred to select those salts which, upon administration, produce a slight systemic alkalinization.

The alkalinizing potassium salts which may be thus administered are preferably selected from the group consisting of potassium bicarbonate ($KHCO_3$) and potassium salts of carboxylic acids such as potassium gluconate ($C_6H_{11}KO_7$) and potassium citrate ($C_6H_5K_3O_7$). The use of potassium bicarbonate is particularly preferred. The preparation, isolation and purification of these salts are well known to those skilled in the art, as they are commonly employed in a therapeutic setting for a variety of uses other than described herein. Specific preparation procedures for each salt are described in general terms in Remington's Pharmaceutical Sciences, Mack Publishing Company, Easton, Pa., 16th Ed., 1982, which is incorporated herein by reference.

Administration of a non-halide alkalinizing potassium salt as an active compound may be in a pharmaceutical composition described hereinafter and can be via any of the accepted modes of administration for agents which are known to affect hypertension or osteoporosis. These methods include oral, parenteral, and other modes of systemic administration. Different non-halide alkalinizing potassium salts may be admixed and simultaneously administered, or benefit may be gained in some instances by their administration in separate dosage forms on different specific schedules.

Depending on the intended mode, the compositions may be in the form of solid, semi-solid or liquid dosage forms, such as, for example, tablets, capsules, pills, powders, granules, crystals, liquids, suspensions, or the like, preferably in unit-dosage forms suitable for administration of relatively precise dosages. The compositions may include a conventional pharmaceutical carrier or excipient and, in addition, may include other pharmaceutical agents, carriers, etc.

The non-halide alkalinizing potassium salt is administered in an amount sufficient to effectively treat both hypertension and osteoporosis but not sufficient to induce undesirable toxic effects in the person treated. The effective amount will, of course, be dependent on the subject being treated, the severity of the affliction, the manner of administration, and the judgment of the prescribing physician. An effective dose of potassium bicarbonate, for instance, will be in the range of 30–180 mmoles/60 kg body weight/day, preferably 60 to 120 mmoles/60 kg/day. Dosages may be adjusted by monitoring the effects of the amount administered and adjusting subsequent amounts as appropriate.

Many of the potassium salts used in the practice of this invention may be administered in relatively large amounts without serious side effects, although indiscriminate use of potassium salts may produce toxic manifestations of hyperkalemia and gastrointestinal irritation. In cases where the compound is administered to prevent the emergence of osteoporosis and hypertension in normotensive subjects susceptible to osteoporosis and hypertension, or those suffering from only mild or borderline osteoporosis and hypertension, the dose may be adjusted accordingly to lower maintenance levels.

For solid compositions, the non-halide potassium salts such as potassium bicarbonate may be provided separately or may be compounded with conventional nontoxic solid carriers such as, for example, pharmaceutical grades of mannitol, lactose, starch, magnesium stearate, talcum, cellulose, glucose, sucrose, magnesium carbonate, and the like. Liquid pharmaceutically-administrable compositions can be prepared, for example, by dissolving the salt, such as potassium bicarbonate, and optional pharmaceutical adjuvants in a carrier, such as, for example, water, aqueous dextrose, glycerol, and the like, to thereby form a solution or suspension. If desired, the pharmaceutical composition to be administered may also contain minor amounts of nontoxic auxiliary substances such as pH buffering agents and the like, for example, sorbitan monolaurate, triethanolamine, sodium acetate, triethanolamine oleate, etc. Actual methods of preparing such dosage forms are known, or will be apparent, to those skilled in this art; see, for example, the aforesaid Remington's Pharmaceutical Sciences, Mack Publishing Company, Easton, Pa., 16th Ed., 1982. The composition or formulation to be administered will, in any event, contain a quantity of the non-halide alkalinizing potassium salt in an effective amount.

For oral administration, a pharmaceutically-acceptable nontoxic composition is formed by the incorporation of any of the normally employed excipients such as, for example, pharmaceutical grades of mannitol, lactose, starch, magnesium stearate, talcum, cellulose, glucose, sucrose, magnesium carbonate, and the like. Such compositions take the form of solutions, suspensions, tablets, pills, capsules, powders, granules, crystals, sustained-release formulations, and the like. Such compositions may contain about 10–100% active ingredient, preferably about 25–90%. As a dietary supplement potassium bicarbonate, for example, may be supplied as pills, as granules or powder applied directly to foodstuffs, or dissolved in drinking water, as convenient means of administration.

The following examples summarize clinical studies which have been carried out employing one of the non-halide alkalinizing potassium salts, potassium bicarbonate, with two groups of subjects. The first group comprised 18 postmenopausal, normotensive women, whereas the second group comprised 54 patients of both sexes, ages 31–66, who had essential hypertension. As summarized below, the data shows that the administration of potassium bicarbonate to these disparate groups of subjects improved both calcium balances and/or calcium excretion, and lowered blood pressures significantly in both groups.

EXAMPLE 1

Figure 2:
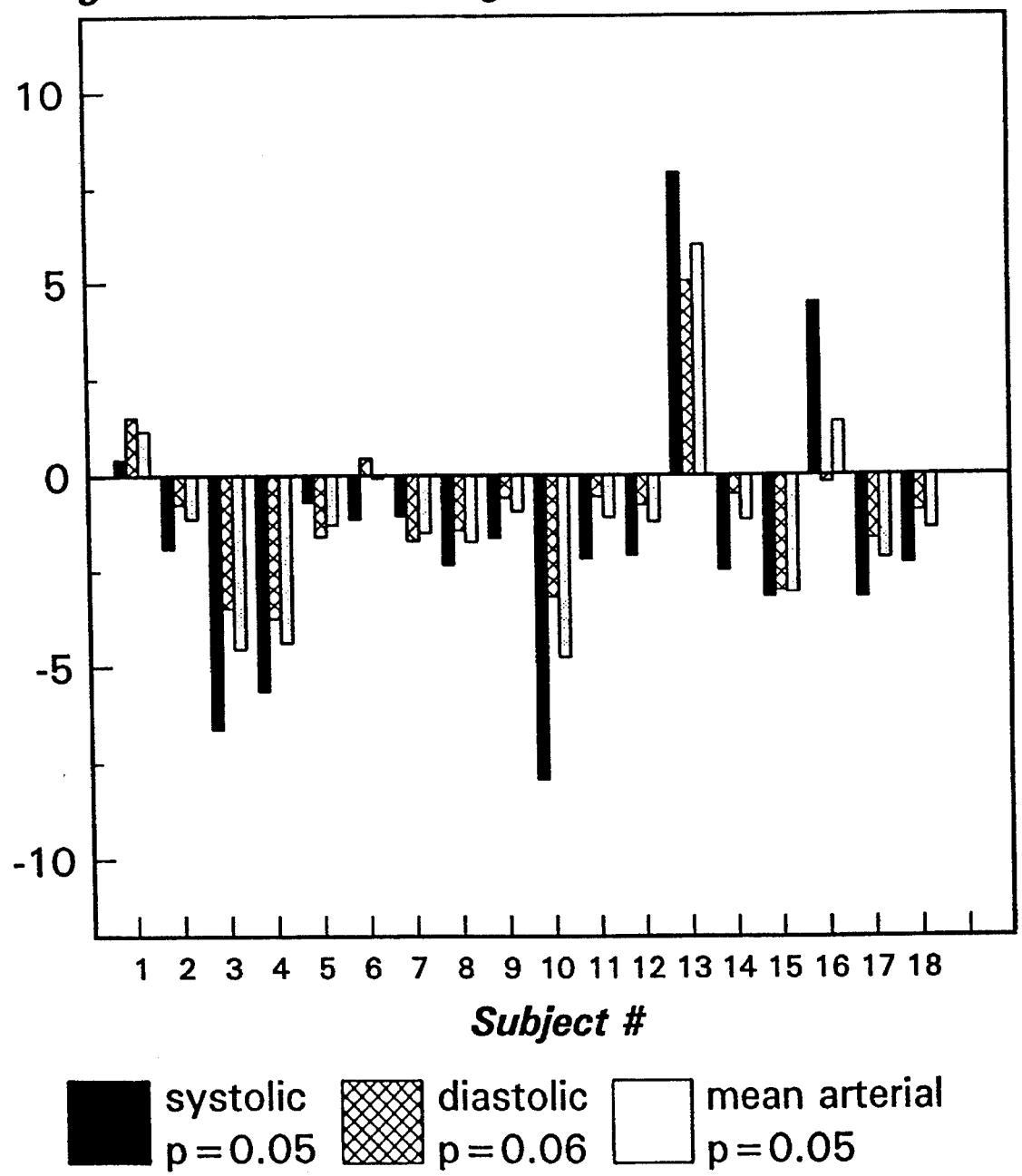
FIG. 2 is a graph showing the changes in blood pressure resulting from the foregoing treatment of the test group of post-menopausal normotensive female subjects.
Figure 3:
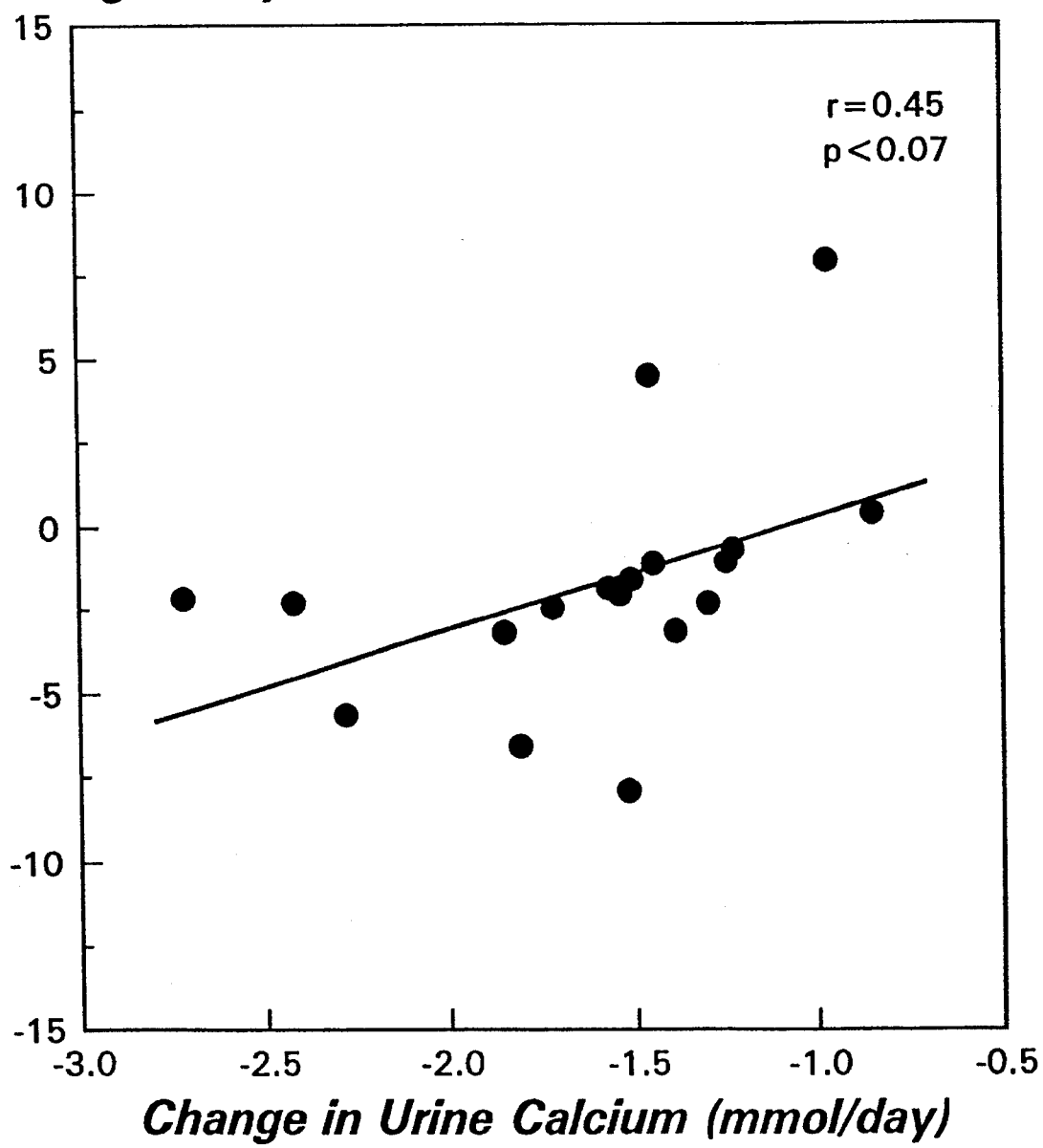
FIG. 3 is a graph showing the relationship between the changes in systolic blood pressure and urine calcium excretion resulting from the foregoing treatment of the test group of postmenopausal normotensive female subjects.
Figure 4:
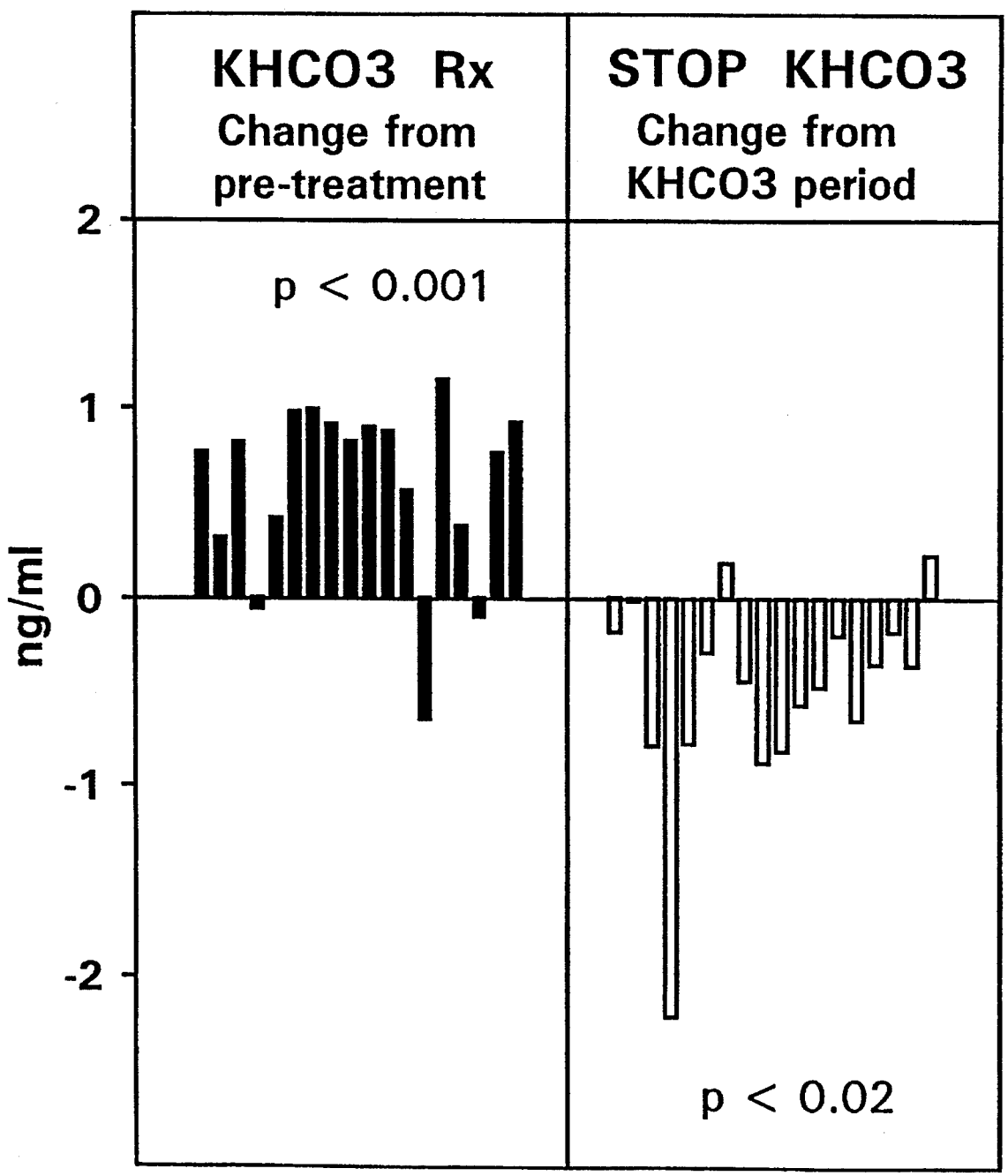
FIG. 4 is a graph showing the change in serum osteocalcin concentration, expressed as the change from the corresponding pre-treatment control values, resulting from the administration of 60–120 mmoles of potassium bicarbonate per 60 kg body weight per day for 18 days to 18 postmenopausal normotensive female subjects (left-hand panel). Also shown is the response when potassium bicarbonate is subsequently withheld (right-hand panel).

Effect of Potassium Bicarbonate on Calcium Balance and on Blood Pressure in Post-Menopausal, Normotensive Women In the postmenopausal, normotensive female test group, the administration of potassium bicarbonate, 60–120 mmoles per 60 kg body weight per day for 18 days, caused a significant reduction in urine calcium and increase in calcium balance (see FIG. 1), and a significant reduction in the three major blood pressure variables (see FIGS. 2 to 4). In particular, calcium balance increased +66±23 (sem) mg/day/60 kg body weight (statistically, significantly different from zero at the p=0.011 level). Concurrently, significant reductions in systolic pressure (mm Hg), −2.0±0.9 (p=0.043), diastolic pressure, −1.1±0.47 (p=0.03) and mean arterial pressure, −1.7±0.6 (p=0.01) were obtained [p values refer to differences from zero].

The studies were performed while the subjects were inpatients at the University of California General Clinical Research Center (Moffitt Hospital). Throughout the period of residence, the subjects ate a constant diet of known composition, comprising (per 60 kg body weight), 500–1000 mg calcium, 948 mg phosphorus, 50 meq sodium and 56 meq potassium. A sodium chloride supplement of 60 mmoles/day was provided, making a total salt intake of 120 meq per 60 kg body weight per day, within the range of a normal salt diet. Fluid intake was fixed.

The subjects were allowed ten days for their bodies to equilibrate and adapt to the fixed diet. Then, following immediately and in succession, the subjects underwent (1) a twelve-day control period (CONTROL), (2) an 18-day period of potassium bicarbonate administration, and (3) a 12-day recovery period after discontinuing the potassium bicarbonate.

FIG. 1 shows the changes in urine calcium excretion, calcium balance, and stool calcium excretion for the group of 18 subjects. For each subject, the average value of calcium excretion for the entire control period was subtracted from each day's urine calcium excretion, thereby generating a "change from control" value for each day of the study. For each subject, the average of the changes from control for the period of potassium bicarbonate administration is plotted as a separate point on the graph. Similarly, the graph shows the changes from control values for calcium balance and stool calcium excretion during the period of potassium bicarbonate administration for each subject.

Potassium bicarbonate administration resulted in a reduction in urine calcium excretion in each subject. Stool calcium excretion did not change consistently among the subjects, averaging close to zero for the group as a whole. Therefore, the improvement in calcium balance shown in FIG. 1 was determined primarily by the reduction in urine calcium excretion caused by the administration of potassium bicarbonate.

The magnitudes of the individual changes in blood pressure against the corresponding changes in urine calcium excretion in each subject for the group as a whole were calculated by regression and correlation analyses, the results being shown in FIG. 3 for systolic blood pressure. There was a significant positive relationship between the two parameters, indicating that the magnitude of the reduction in systolic blood pressure resulting from potassium bicarbonate administration correlated positively with the magnitude of the reduction in urine calcium excretion among the subjects (r=0.45, p<0.07). A similar correlation was observed for diastolic pressure and calcium excretion (r=0.41, p<0.09), and for mean arterial pressure and calcium excretion (r=0.44, p<0.07). This demonstrates that in postmenopausal women potassium bicarbonate's potency for the prevention or treatment of osteoporosis is related to its potency in respect of its ability to lower blood pressure.

Figure 5:
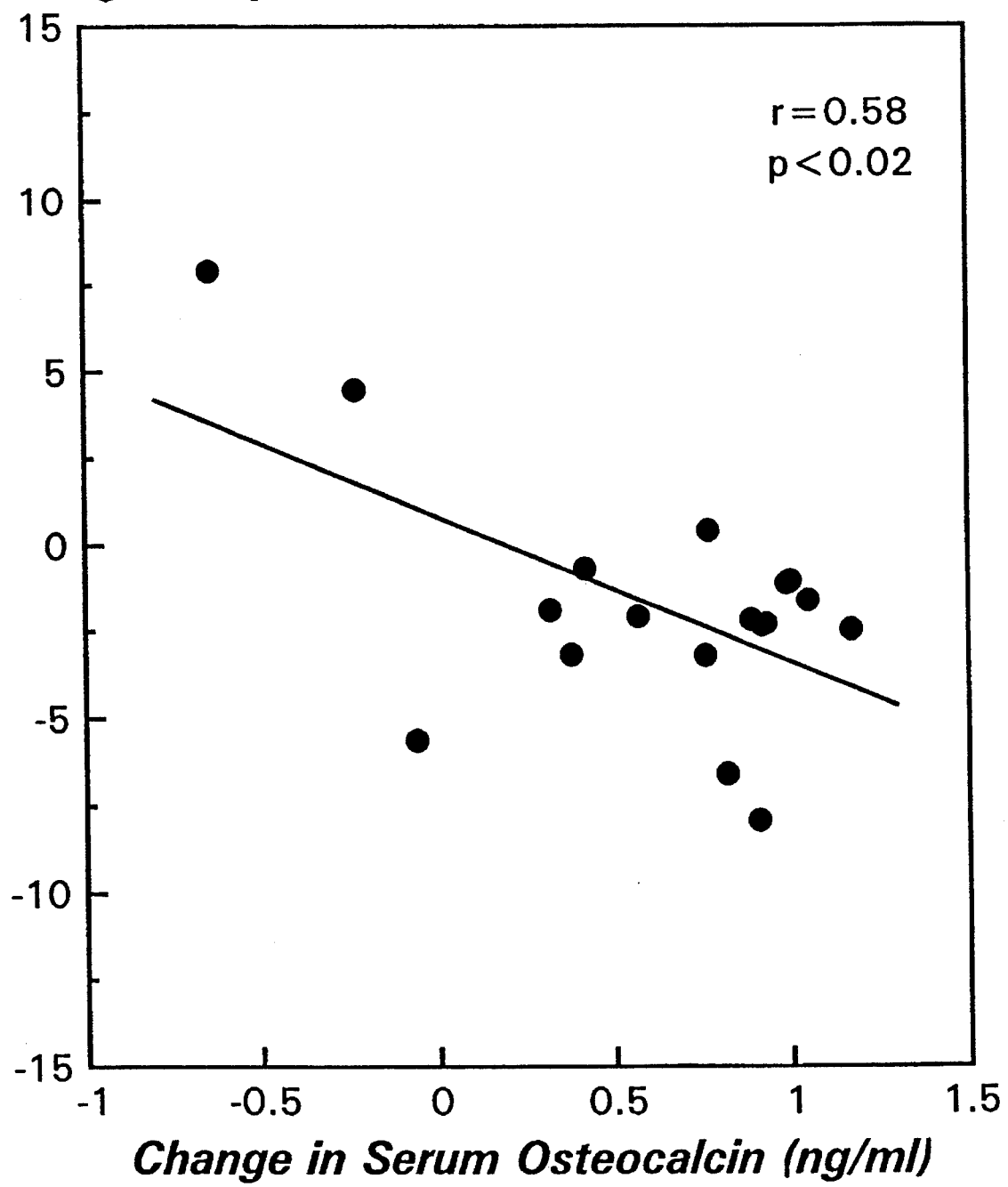
FIG. 5 is a graph showing the relationship between the changes in systolic blood pressure and serum osteocalcin concentration resulting from the foregoing treatment of the test group of post-menopausal normotensive female subjects.

This conclusion is further supported when the relationship between potassium bicarbonate's blood pressure-lowering ability and its ability to increase serum osteocalcin concentration is examined. Serum osteocalcin is a marker of the rate of bone formation. Osteocalcin is an integral protein of the organic matrix of bone, synthesized by bone-forming cells (osteoblasts) during the process of bone formation. A small fraction of the newly synthesized osteocalcin leaks into the systemic circulation where its concentration in serum serves as a biochemical marker of the rate of bone formation, increasing when the rate of bone formation increases and decreasing when the rate of bone formation decreases. The administration of potassium bicarbonate resulted in an increase in osteocalcin concentration in the postmenopausal women studied as shown in FIG. 4. The magnitude of that increase correlated with the reduction in blood pressure as shown in FIG. 5 (r=0.58, p<0.02). Again, in postmenopausal women, the potency of potassium bicarbonate for the prevention or treatment of osteoporosis is related to its potency in respect of its ability to lower blood pressure.

EXAMPLE 2

Figure 6:
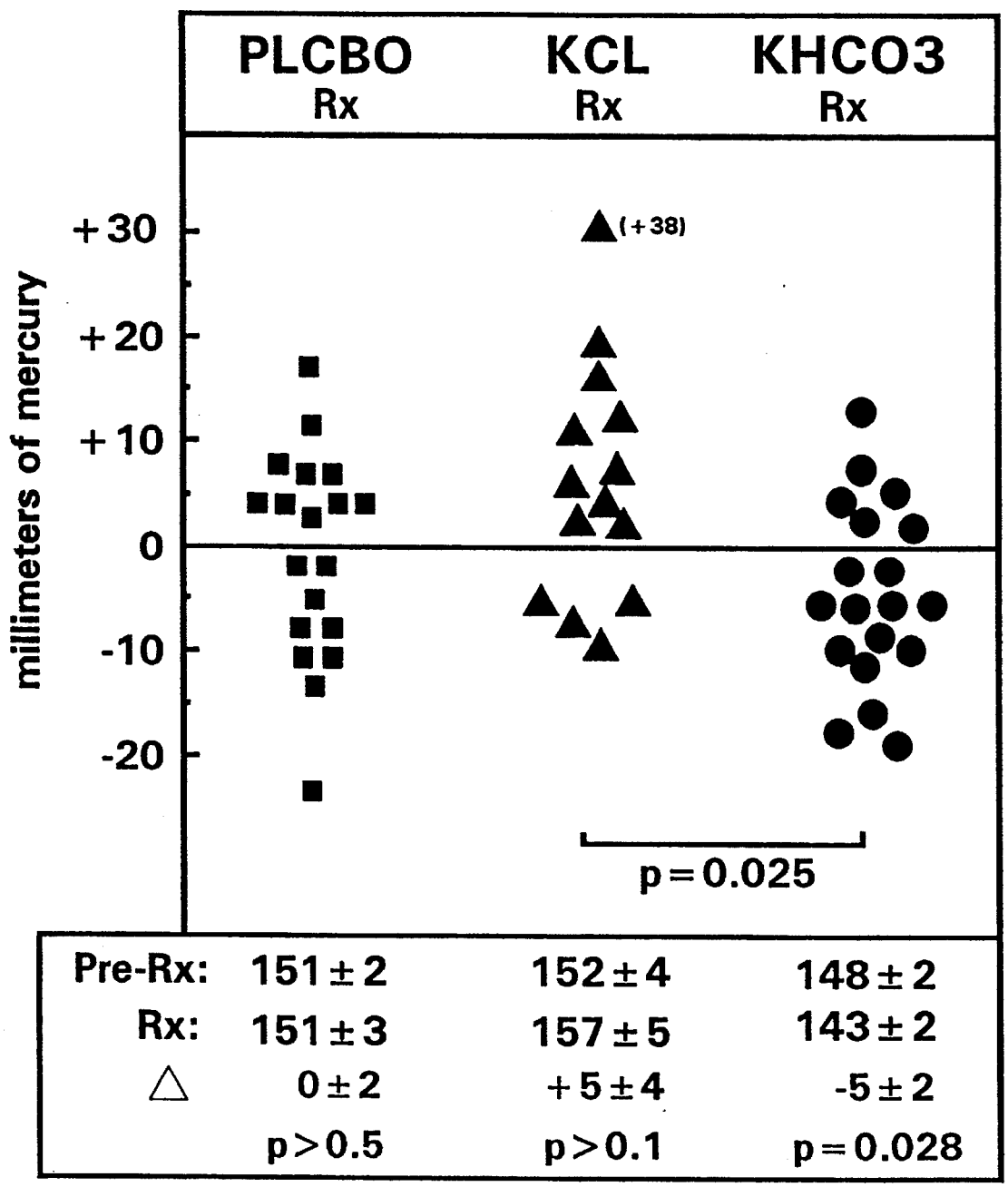
FIG. 6 is a graph showing the changes in systolic pressure from the average pre-treatment values in three groups of patients having essential hypertension, whose diets were supplemented with potassium bicarbonate, potassium chloride or a placebo.
Figure 7:
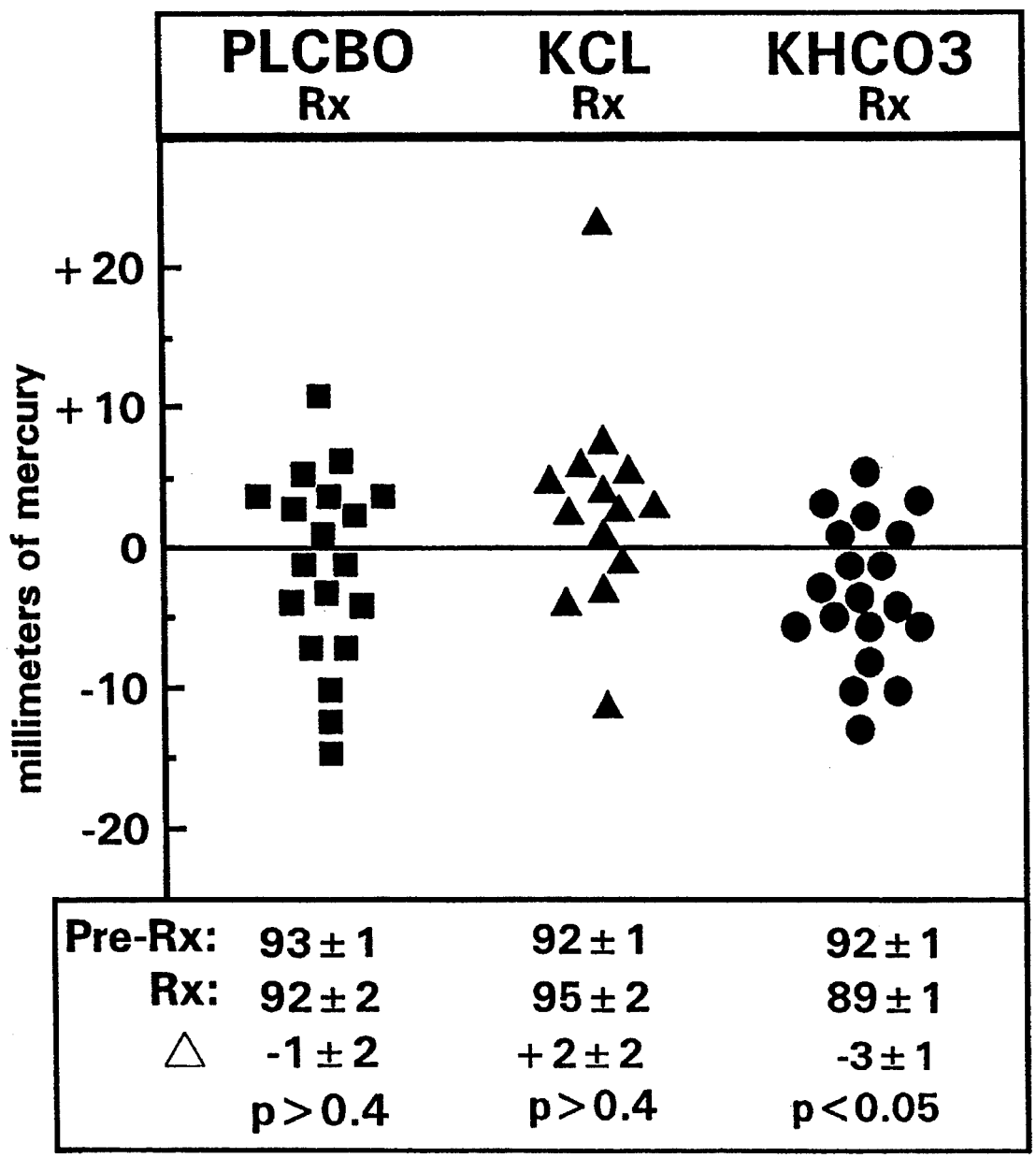
FIG. 7 is a graph similar to FIG. 6, showing the change in diastolic pressure from the average pre-treatment value in the same three groups of hypertensive patients referred to hereinabove.

Comparative Effect of Administration of Potassium Bicarbonate and Potassium Chloride on Urine Calcium Excretion and Blood Pressure in Patients With Essential Hypertension In those patients treated who had essential hypertension, it was found that the administration of potassium bicarbonate but not potassium chloride, caused significant reduction in urine calcium excretion (see FIG. 8) and in both systolic and diastolic blood pressure (see FIGS. 6 and 7).

The studies were carried out on an out-patient basis in patients with essential hypertension between the ages of 31 and 66 years who received no anti-hypertensive medications for at least four weeks prior to enrollment in the study, ,and whose average diastolic pressure was between 87 and 104 mm Hg on their final two consecutive pre-treatment visits. In double-blind fashion, the subjects were randomly assigned to one of three treatment groups: (1) placebo (PLCBO), (2) potassium chloride (KCL), 60 to 90 mmoles per day, and (3) potassium bicarbonate (KHCO3), 60 to 90 mmoles per day. The duration of the study per patient was twenty-eight weeks; six weeks for pre-treatment, sixteen weeks on treatment, followed by six weeks of withdrawal from the treatment. Patients returned for evaluation at weeks zero, 2, 4, 6, 8, 10, 12, 16, 20, 22, and 26. The patients' diets and activities did not differ from their usual routines.

All clinic visits occurred between 2:00 P.M. and 7:00 P.M., with the exact time of each patient's visit maintained constant. Blood pressure was measured with the patient sitting, not less than sixty minutes after the last intake of food or smoke, and after at least. 15 minutes of quiet sitting. An automatic oscillometric device (a Dinamap automatic blood pressure recorder) was used to measure the blood pressure in the patients' non-dominant arms. At selected intervals during each study phase, the patients collected 24-hour urine samples which they brought to the clinic.

The results of the study are shown in FIGS. 6–7, wherein the individual data points represent the patients treated with the placebo (the squares in the figures), with potassium chloride (the triangles in the figures) and with potassium bicarbonate (the circles in the figures). The results for both the urine calcium excretion and blood pressure variables (systolic and diastolic blood pressures) are presented in terms of the "Change from Pre-RX" (the average pre-treatment value), each data point representing a different patient. Two different statistical analyses were performed. The results of the first type of statistical analysis, shown in the rectangle below each figure, show for each treatment whether the changes from pre-treatment were significantly different from zero. The triangle symbol stands for "delta", which is the magnitude of the change from pretreatment to treatment. The values are means±SEM. The results of the second type of statistical analysis, shown in the lower half of the figure as a horizontal square-bracket, show whether, considering all possible pairs, any two groups showed a significantly different response from each other.

Figure 8:
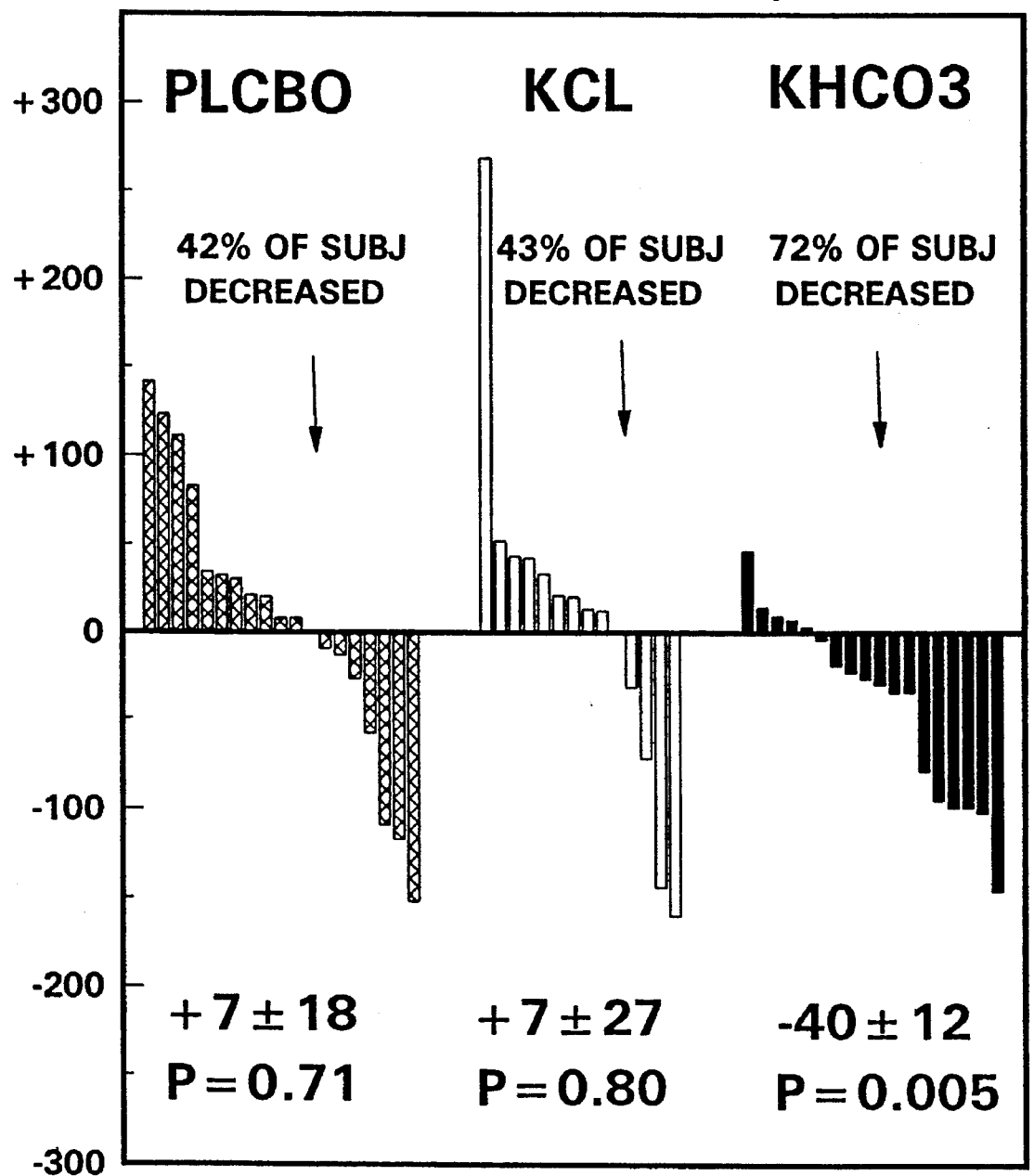
FIG. 8 is a graph showing the changes in urine calcium excretion from the average pre-treatment values in the same three groups of hypertensive patients referred to hereinabove.

FIG. 8 demonstrates that treatment with potassium bicarbonate resulted in significant reductions in urine calcium excretion, whereas no significant reductions in urine calcium excretion occurred in patients treated with potassium chloride or with a placebo. FIG. 6 demonstrates that significant reductions in systolic blood pressure also occurred only in patients treated with potassium bicarbonate. Similarly, as shown in FIG. 7, significant reductions in diastolic blood pressure occurred only in patients treated with potassium bicarbonate. Thus, patients with essential hypertension who were treated with potassium bicarbonate had significant reductions in both urine calcium excretion and blood pressure, whereas the patients treated with KCl or the placebo had no such reductions.

The preceding examples demonstrate that the administration of potassium bicarbonate to either normotensive or hypertensive subjects, or to postmenopausal or other subjects, both decreases urinary calcium excretion (and thus improves calcium balance) and blood pressure.

Although the present invention has been described in some detail by way of illustration and example for purposes of clarity and understanding, it will be obvious that certain changes and modifications may be practiced within the scope of the appended claims.

What is claimed:

1. A method for the simultaneous treatment of both hypertension and osteoporosis in a person who has or is susceptible to both such diseases and who is on a diet having a normal range of salt content, comprising orally administering to such person a composition containing a major amount of potassium bicarbonate as the principal active ingredient for the simultaneous treatment of hypertension and osteoporosis, the potassium bicarbonate being administered in an amount sufficient to have a measurable effect upon both hypertension and osteoporosis, which can be shown experimentally to be due to the presence of potassium bicarbonate, but not sufficient to induce undesirable toxic effects.

2. The method of claim 1, wherein the potassium bicarbonate is administered in an amount sufficient to improve calcium and phosphorus balance, decrease bone resorption, conserve and/or increase bone mass, and decrease blood pressure.

3. The method of claim 1, wherein the composition is substantially free of sodium bicarbonate.

4. The method of claim 1, wherein the potassium bicarbonate is administered in an amount of from about 30 to 180 mmoles/60 kg body weight/day or at a lower maintenance level for preventing the emergence of hypertension and osteoporosis in a person susceptible to hypertension and osteoporosis or to a person suffering from only mild or borderline hypertension and osteoporosis.

5. The method of claim 1, wherein the composition is administered as a dietary supplement.

6. The method of claim 1, wherein the potassium bicarbonate is substantially the only active ingredient for treating hypertension and osteoporosis in the composition.

7. The method of claim 6, wherein the composition is substantially free of sodium bicarbonate.

8. The method of claim 1, wherein the person treated has essential hypertension.

9. The method of claim 1, wherein the composition is administered to a postmenopausal woman.

* * * * *